(12) United States Patent
Giambattista et al.

(10) Patent No.: US 8,827,962 B2
(45) Date of Patent: *Sep. 9, 2014

(54) MEDICAMENT DELIVERY DEVICE

(71) Applicant: SHL Group AB, Nacka Strand (SE)

(72) Inventors: Lucio Giambattista, East Hannover, NJ (US); Antonio Bendek, Vernon, NJ (US)

(73) Assignee: SHL Group AB, Nacka Strand (SE)

(*) Notice: Subject to any disclaimer, the term of this patent is extended or adjusted under 35 U.S.C. 154(b) by 0 days.

This patent is subject to a terminal disclaimer.

(21) Appl. No.: 13/896,639

(22) Filed: May 17, 2013

(65) Prior Publication Data

US 2013/0274681 A1    Oct. 17, 2013

Related U.S. Application Data

(63) Continuation of application No. 13/203,040, filed as application No. PCT/US2010/060022 on Dec. 13, 2010, now Pat. No. 8,491,536.

(30) Foreign Application Priority Data

Dec. 15, 2009 (SE) ................................ 0950958-9

(51) Int. Cl.
| | | |
|---|---|---|
| A61M 5/00 | (2006.01) | |
| A61M 5/178 | (2006.01) | |
| A61M 5/24 | (2006.01) | |
| A61M 5/315 | (2006.01) | |

(52) U.S. Cl.
CPC ... *A61M 5/31551* (2013.01); *A61M 2005/2407* (2013.01); *A61M 5/31561* (2013.01); *A61M 5/3158* (2013.01); *A61M 5/24* (2013.01); *A61M 5/31553* (2013.01)
USPC ............................ 604/209; 604/181; 604/186

(58) Field of Classification Search
CPC .............. A61M 5/24; A61M 5/31575; A61M 5/31551; A61M 2205/581; A61M 2005/2488; A61M 5/3158; A61M 5/3155
USPC .................................. 604/181, 186, 207–211
See application file for complete search history.

(56) References Cited

U.S. PATENT DOCUMENTS

| | | |
|---|---|---|
| 6,042,571 A | 3/2000 | Hjertman et al. |
| 6,221,053 B1 | 4/2001 | Walters et al. |

(Continued)

FOREIGN PATENT DOCUMENTS

| | | |
|---|---|---|
| DE | 102004063652 | 7/2006 |
| WO | 01/95959 | 12/2001 |
| WO | 03/080160 | 10/2003 |
| WO | 2008/101829 | 8/2008 |

OTHER PUBLICATIONS

International Search Report and Written Opinion for International Patent App. No. PCT/US2010/060022.

*Primary Examiner* — Rebecca E Eisenberg
(74) *Attorney, Agent, or Firm* — McDonnell Boehnen Hulbert & Berghoff LLP

(57) ABSTRACT

A dose setting mechanism for a medicament delivery device is presented having a pinion mounted to a locking member where the axis of rotation of the pinion is offset and parallel to the longitudinal axis of the housing containing the dose setting components. Primary and secondary dose members are engaged with the pinion to indicate a set dose of medicament.

14 Claims, 8 Drawing Sheets

(56) References Cited

U.S. PATENT DOCUMENTS

| | | |
|---|---|---|
| 2005/0165363 A1 | 7/2005 | Judson et al. |
| 2009/0275914 A1 | 11/2009 | Harms et al. |
| 2009/0275916 A1 | 11/2009 | Harms et al. |
| 2011/0306947 A1 | 12/2011 | Boyd et al. |
| 2012/0283648 A1 | 11/2012 | Veasey et al. |
| 2012/0302964 A1 | 11/2012 | MacDonald et al. |

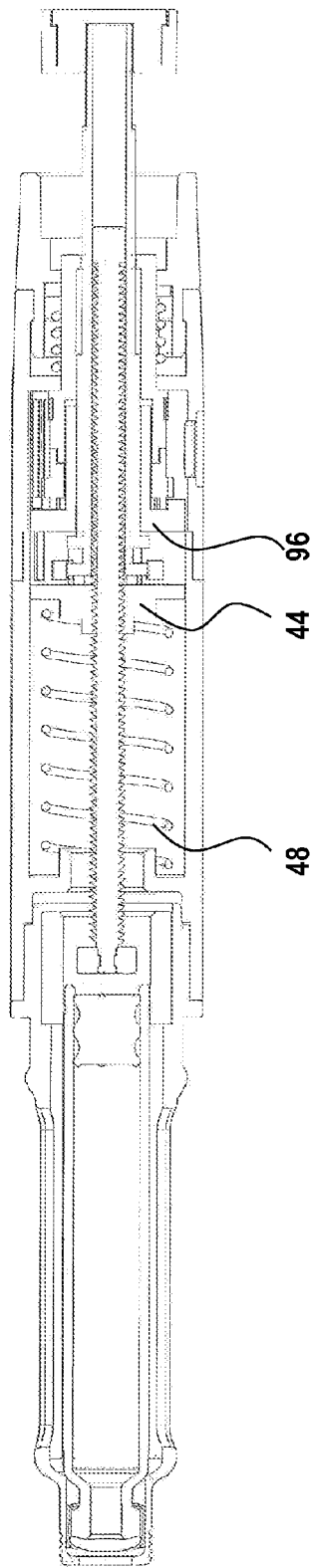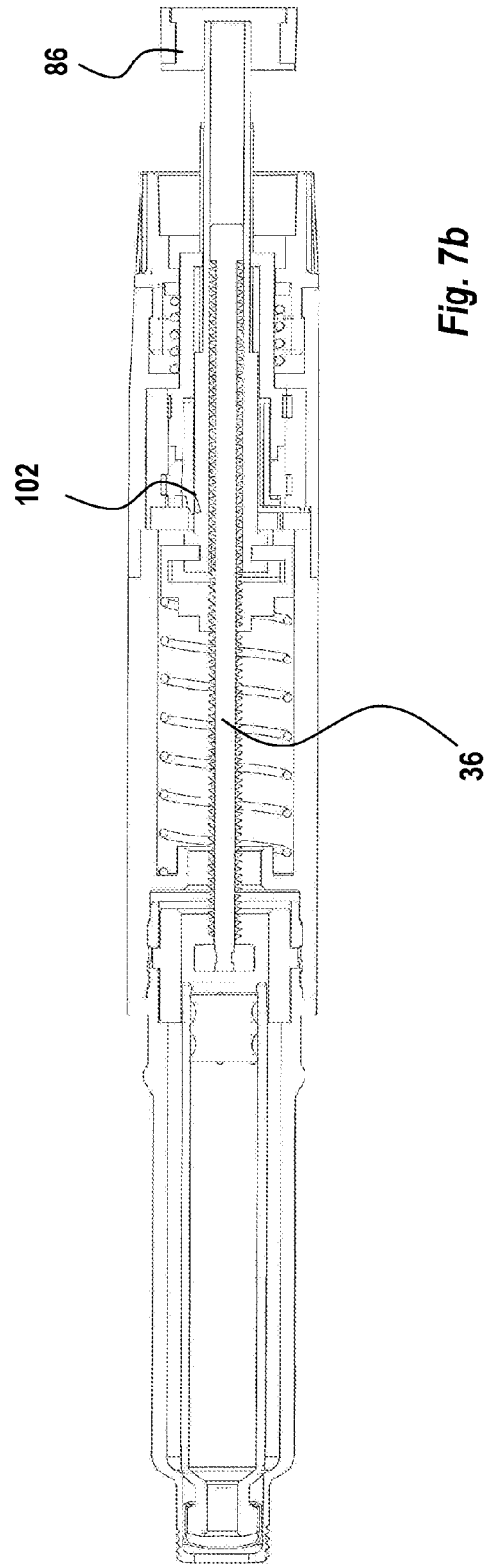
Fig. 7a
Fig. 7b

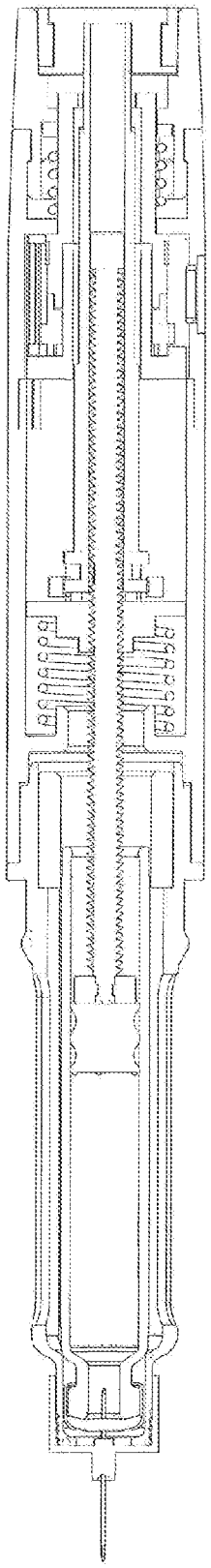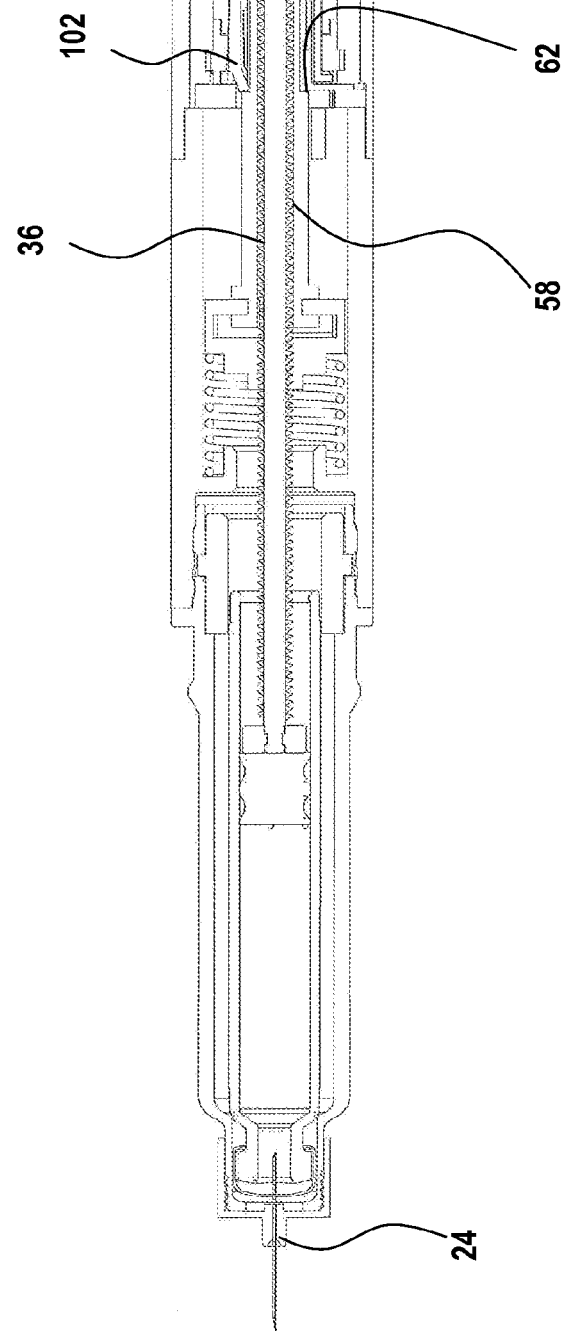
Fig. 8a
Fig. 8b

MEDICAMENT DELIVERY DEVICE

CROSS REFERENCE TO RELATED APPLICATIONS

The present application is a continuation U.S. patent application Ser. No. 13/203,040, filed Jan. 31, 2012, which is a U.S. National Phase Application pursuant to 35 U.S.C. §371 of International Application No. PCT/US2010/060022 filed Dec. 13, 2010, which claims priority to Swedish Patent Application No. 0950958-9 filed on Dec. 15, 2009. The entire disclosure contents of these applications are herewith incorporated by reference into the present application.

TECHNICAL AREA

The present invention relates to a medicament delivery device comprising a dose setting function.

BACKGROUND

Medicament delivery devices such as injectors are sometimes provided with functions where a specific dose can be set by the user, which dose may be varied within a range.

Quite often this dose setting function is performed by turning a knob or wheel at the distal end of the device whereby it is moved in the distal direction. When performing a subsequent injection, the knob is pushed linearly in the proximal direction. One such injector is disclosed in the document U.S. Pat. No. 6,221,053 in which the distal dose knob of the injector is threaded out of a rod barrel tube as a dose is set. Thus the distance the knob is moved in the distal direction is directly related to the dose quantity to be delivered.

One drawback with that type of solution is that if larger doses are to be delivered the dose knob has to be moved quite a long distance in the distal direction, which means that it might be difficult for a user to push the dose knob in the proximal direction during injection.

SUMMARY

The aim of the present invention is to remedy the drawbacks of the state of the art medicament delivery devices and to provide a device by which it is possible to set a desired or required dose in a simple and intuitive way.

This aim is obtained by a medicament delivery device according to the features of the independent patent claim. Preferable embodiments of the invention are subject of the dependent patent claims.

According to a main aspect of the invention it is characterised by a medicament delivery device comprising a housing having opposite distal and proximal ends; a medicament container holder releasably connected to said housing; a medicament container arranged inside said medicament container holder; a threaded plunger rod arranged to pass through a first inner wall of the housing and arranged to act on a stopper in the medicament container; a lead screw member coaxially connected to the threaded plunger rod by co-acting first slidably-and-rotatably-locked means; wherein said device further comprises a nut coaxially connected to the threaded plunger rod by a treaded engagement between them, connected to the lead screw member by co-acting non-slidable-and-rotatable means, and connected to the housing by co-acting second slidably-and-rotatably-locked means; a primary dose member coaxially rotatable on the lead screw member when the device is in a non-activated state and connected to the lead screw member by co-acting third slidably-and-rotatably-locked means when the device is in an activated state; a locking member fixedly connected to the housing and releasably connected to the lead screw member by co-acting locking means; a first spring force means arranged between the first inner wall of the housing and the nut, wherein the first spring force means is in a pre-tensioned state when said locking means are engaged and the device is in the non-activated state; a secondary dose member rotatably connected to said primary dose member via a pinion gear; dose setting means connected to the primary dose member by co-acting fourth slidably-and-rotatably-locked means, such that when the device is to be set from the non-activated state to the activated state, the dose setting means are manually manipulated in a pre-determined direction, whereby the locking means are released and the lead screw member is distally moved a pre-determined distance by the first spring force means independent of the size of a dose to be set.

According to a further aspect of the invention, said primary and said secondary dose members are provided with indicia.

According to another aspect of the invention, the locking means comprises a proximally pointing and radial flexible lever arranged on the locking member, an annular ledge on the circumferential surface of the lead crew member, and the circumferential inner surface of the secondary dose member; such that when the first spring force means is in a pre-tensioned state, the circumferential inner surface of the secondary dose member forces the flexible lever radial inwardly in contact with the ledge; and when the dose setting means are manually manipulated, the secondary dose member is rotated to a position wherein the flexible lever is radial outwardly flexed into a longitudinal groove on the inner circumferential surface of the secondary dose member.

According to yet a further aspect of the invention, the locking member comprises on its distal circumferential surface a distally pointing stop member, and wherein the secondary dose member comprises on its proximal circumferential surface a first and a second proximally pointing stop members arranged to interact with the stop member of the locking member.

According to yet another aspect of the invention, the non-slidable-and-rotatable means comprises ratchet arms and radial inwardly directed arms on the nut, grooves on the outer circumference of wheels on the proximal end of the lead screw member, and an annular groove between the wheels, wherein the ratchet arms cooperate with the grooves for giving an audible signal when the lead screw member is rotated; and wherein the radial inwardly directed arms cooperate with the annular groove such that the lead screw member and the nut are slidably locked and rotatable in relation to each other.

According to a further aspect of the invention, the first slidably-and-rotatably-locked means comprises radial inwardly directed ledges on the inner surface of the proximal end of the lead screw member, and longitudinally extending grooves on the plunger rod, wherein the grooves cooperate with the radial inwardly directed ledges such that the lead screw member and the plunger rod are rotationally locked and slidable in relation to each other.

According to another aspect of the invention, the second slidably-and-rotatably-locked means comprises grooves on the outer circumferential side surface of the nut, and longitudinal ribs on the inner surface of the housing, wherein the grooves cooperate with the longitudinal ribs such that the nut and the housing are rotationally locked and slidable in relation to each other.

According to yet a further aspect of the invention, the third slidably-and-rotatably-locked means comprises splines on the outer circumferential surface of the lead screw member, and corresponding splines arranged on the inner circumferential surface of the primary dose member, wherein the splines cooperate with corresponding splines such that the lead screw member and the primary dose member are rotationally locked and slidable in relation to each other.

According to yet another aspect of the invention, the dose setting means comprises a clutch plate provided with a first annular ratchet, a dose setting knob provided with a second annular ratchet, and a second spring force means arranged between a second inner wall of the housing and a proximal surface of the clutch plate, such that clutch plate is distally urged and the first and the second ratchet are abutting each other, and which dose setting knob protrudes through the distal end of the housing.

According to a further aspect of the invention, the fourth slidably-and-rotatably-locked means comprises longitudinally extending grooves on the outer circumferential surface of the primary dose member, and radial inwardly directed protrusions on the inner surface of the clutch plate, wherein the longitudinally extending grooves cooperate with radial inwardly directed protrusions such that the primary dose member and the clutch plate are rotationally locked and slidable in relation to each other.

According to another aspect of the invention, the plunger rod is arranged to be proximally moved a distance corresponding to a set dose to be delivered by manually manipulating the dose setting knob when the device is in the activated state.

There are a number of advantages with the present invention. Because the lead screw, e.g. the manually operating delivery means, protrudes outside the housing with the same length independent of the set dose quantity the manual dose delivery operation is the same independent of set dose, i.e. the lead screw member has always the same position when a dose has been set.

Compared to the state of the art medicament delivery devices, this solution is a great advantage for the user or patient who suffers of dexterity problems. Also when not in use, the lead screw member is inside the medicament delivery device and locked. The unlocking of the lead screw member is performed when said dose setting knob is turned to an initial position, preferably a zero-dose position.

These and other features and advantages will become apparent from the detailed description and from the accompanying drawings.

BRIEF DESCRIPTION OF THE FIGURES

In the detailed description reference will be made to the accompanying drawings in which FIGS. 1*a*,*b* are a cross-sectional view of a medicament delivery device according to the present invention;

FIGS. 6, 7*a*, 7*b*, 8*a*, and 8*b* are cross-sectional view of different functional positions.

DETAILED DESCRIPTION

Figure 1:
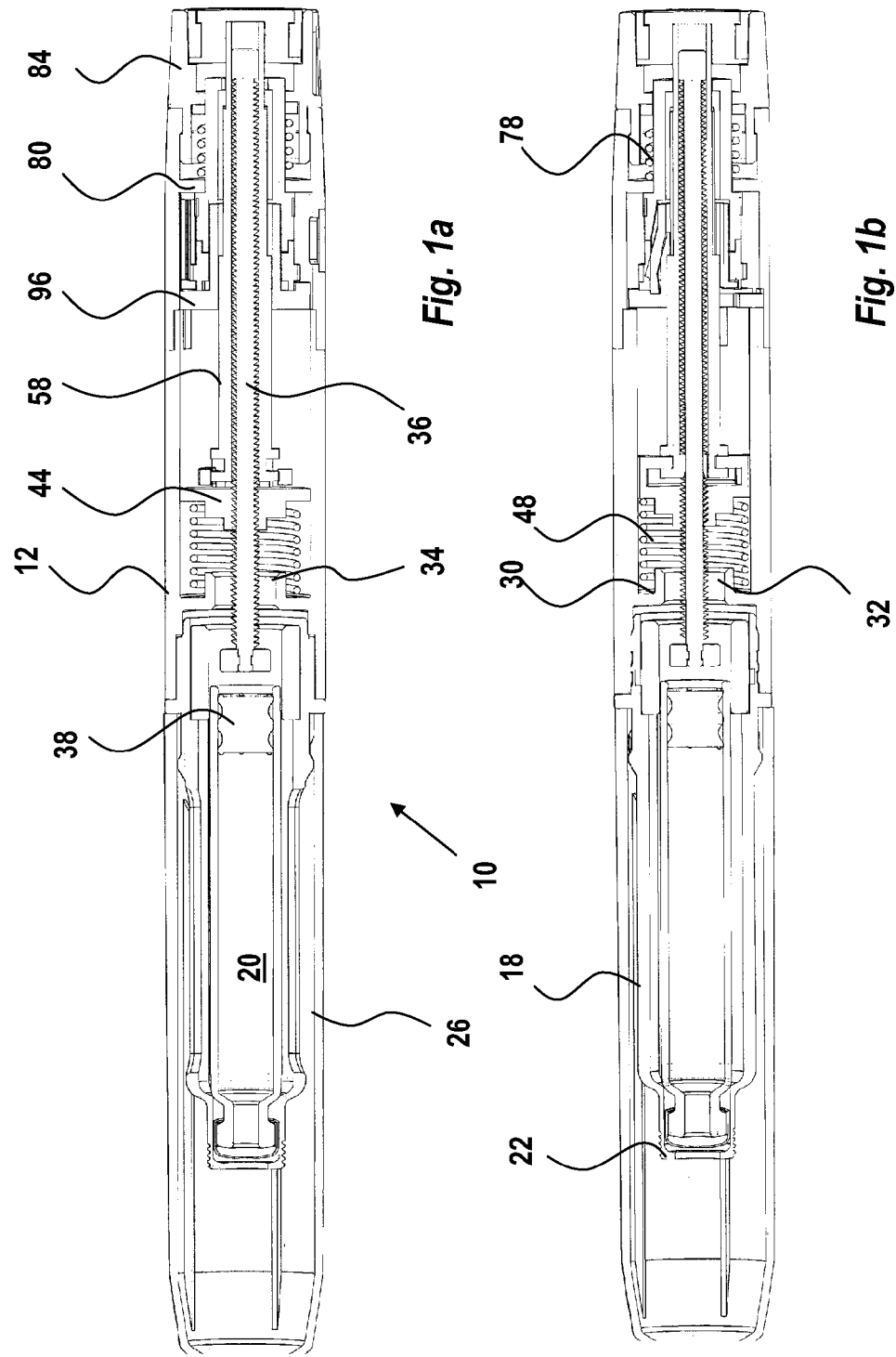

In the present application, when the term "distal part/end" is used, this refers to the part/end of the injection device, or the parts/ends of the members thereof, which under use of the injection device is located the furthest away from the medicament injection site of the patient. Correspondingly, when the term "proximal part/end" is used, this refers to the part/end of the injection device, or the parts/ends of the members thereof, which under use of the injection device is located closest to the medicament injection site of the patient.

The medicament delivery device 10 according to the drawings comprises a generally elongated housing 12 having opposite distal and proximal ends. The elongated housing being e.g. divided in a proximal 12*a* and a distal part 12*b*. The proximal end of the housing is arranged with fastening means such as e.g. threads 14 on its inner surface, which fastening means cooperate with corresponding fastening means such as outwardly threads 16 on a distal end of a medicament container holder 18, providing a releasable connection. Inside the medicament container holder a medicament container 20 can be placed. The proximal end of the medicament container holder 18 is arranged with a threaded neck 22 for connection of a medicament delivery member such as an injection needle 24, a mouthpiece, a nozzle or the like, FIG. 2.

When received by a user, the medicament delivery device 10 is provided with a releasably attachable protective cap 26. At the distal end of the medicament container holder a sleeve-shaped container support 28 is inserted for holding and supporting the medicament container 20 when inserted, FIG. 2. At the proximal end of the housing a first inner wall 30 is arranged, which wall is provided with a central passage 32, FIG. 1*b*. The central passage is arranged with a distally directed tubular flange 34, FIG. 1*a*. A threaded plunger rod 36 extends in the longitudinal direction through the central passage 32 with a proximal end adjacent a stopper 38 inside said medicament container 20, FIG. 1*a*. The proximal end of the plunger rod 36 is further arranged with a plunger rod tip 40, FIG. 2.

The device further comprises a lead screw member 58 coaxially connected to the threaded plunger rod by co-acting first slidably-and-rotatably-locked means; and a nut 44 coaxially connected to the threaded plunger rod by a treaded engagement between them. The nut also being connected to the lead screw member by co-acting non-slidable-and-rotatable means, and to the housing by co-acting second slidably-and-rotatably-locked means.

Figure 2:
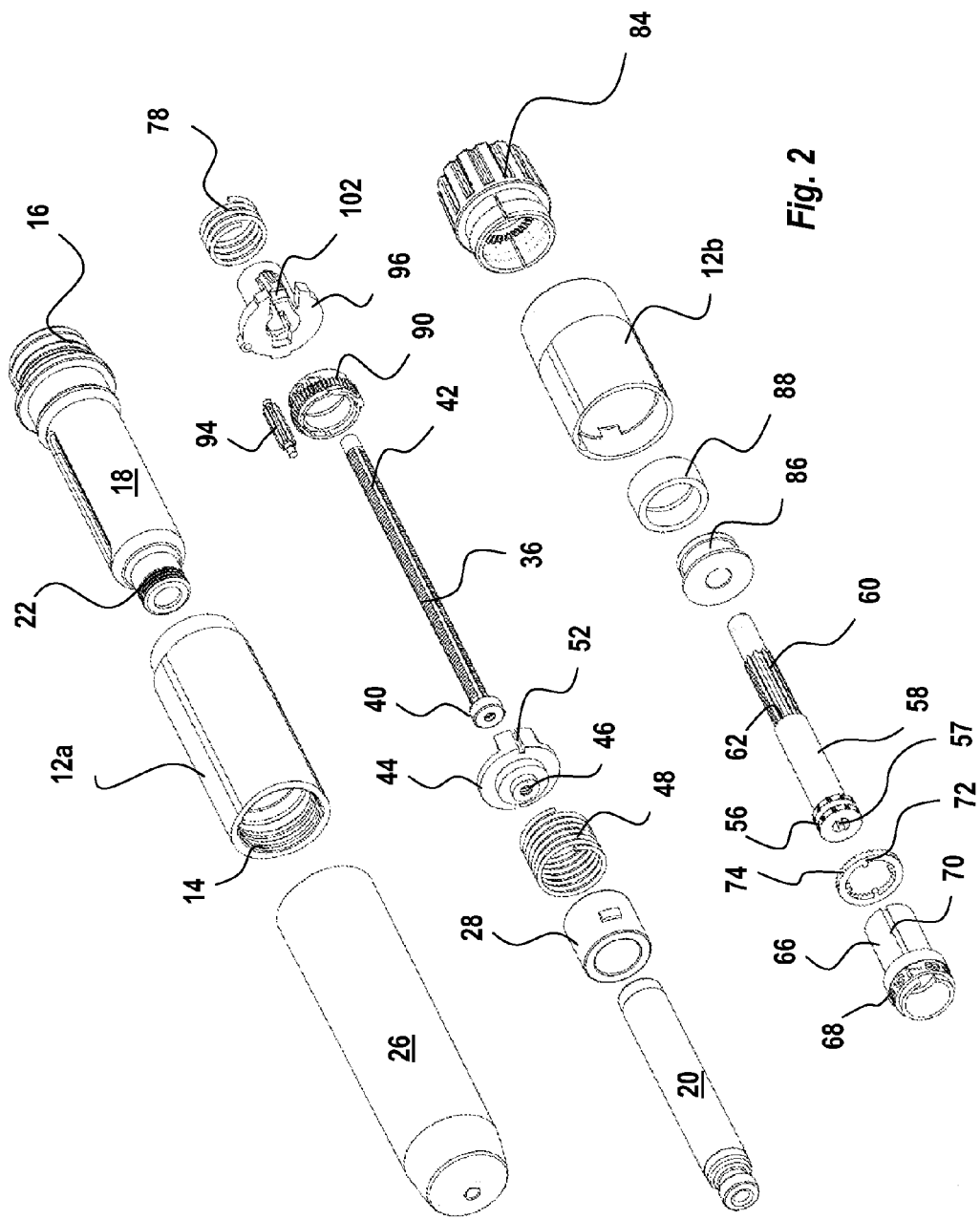
FIG. 2 is an exploded view of the medicament delivery device of FIGS. 1*a*,*b*.

The first slidably-and-rotatably-locked means comprises radial inwardly directed ledges 57 on the inner surface of the proximal end of the lead screw member, and longitudinally extending grooves 42 on the plunger rod, FIG. 2, wherein the grooves cooperate with the radial inwardly directed ledges 57 such that the lead screw member and the plunger rod are rotationally locked and slidable in relation to each other.

Figure 3:
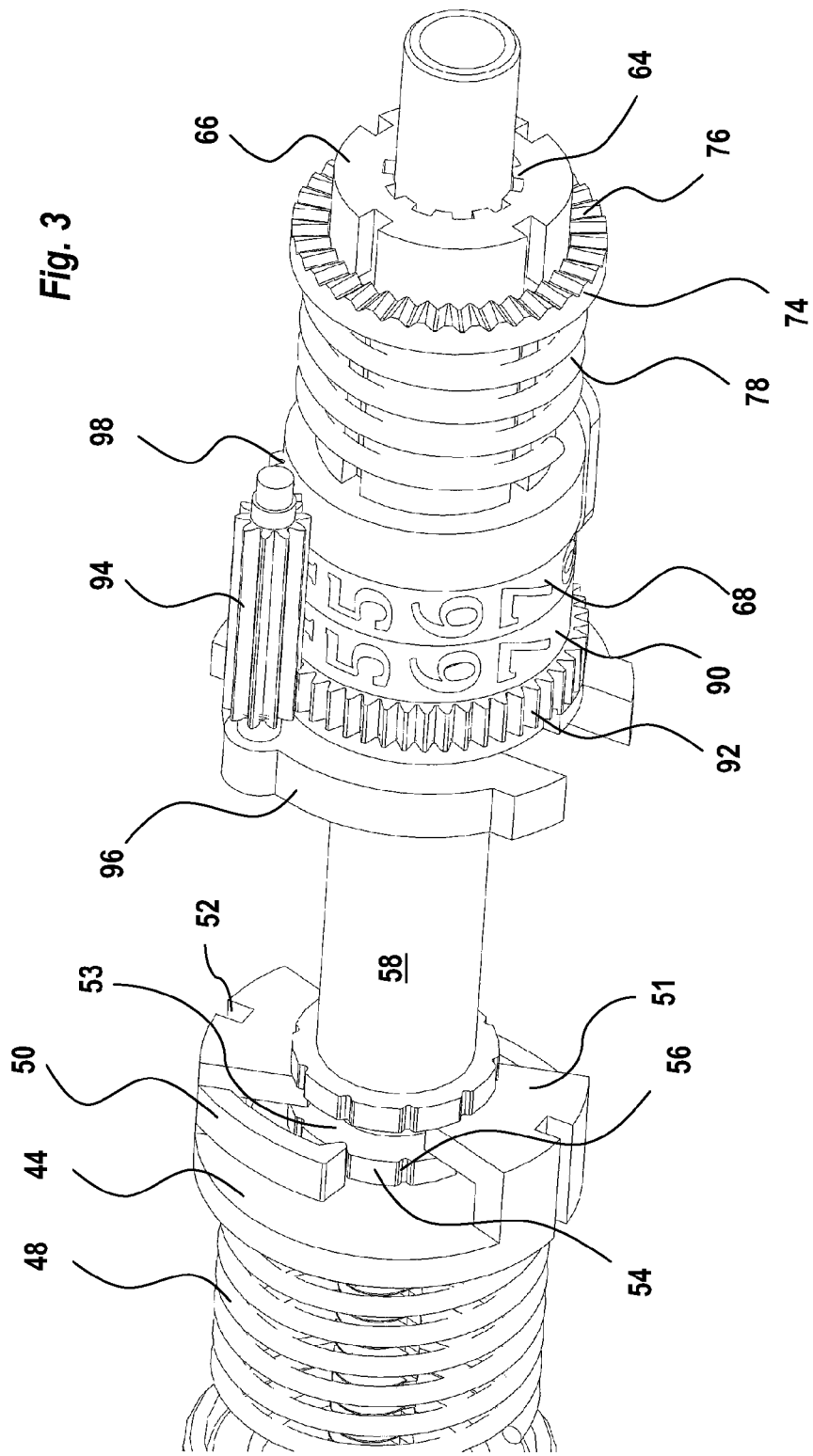
FIG. 3 is a detailed view of a dose-setting mechanism comprised in the present invention.

The non-slidable-and-rotatable means comprises ratchet arms 50 and radial inwardly directed arms 51 on the nut 44, grooves 56 on the outer circumference of wheels 54 on the proximal end of the lead screw member, and an annular groove 53 between the wheels 54, wherein the ratchet arms 50 cooperate with the grooves 56 for giving an audible signal when the lead screw member is rotated; and wherein the radial inwardly directed arms 51 cooperate with the annular groove 53 such that the lead screw member and the nut are slidably locked and rotatable in relation to each other, FIG. 3.

The second slidably-and-rotatably-locked means comprises grooves 52 on the outer circumferential side surface of the nut 44, FIG. 3, and longitudinal ribs on the inner surface of the housing (not shown), wherein the grooves cooperate with the longitudinal ribs such that the nut and the housing are rotationally locked and slidable in relation to each other.

The nut 44 comprises a threaded central passage 46 which cooperates with the threads of the plunger rod, FIG. 2, thereby forming the threaded engagement between them.

The device also comprises a primary dose member 66 coaxially rotatable on the lead screw member when the device is in a non-activated state and connected to the lead screw member by co-acting third slidably-and-rotatably-locked means when the device is in an activated state. The third slidably-and-rotatably-locked means comprises splines 60 on the outer circumferential surface of the lead screw member; and corresponding splines 64 arranged on the inner circumferential surface of the primary dose member, wherein the splines 60 cooperate with corresponding splines 64 such that the lead screw member and the primary dose member are rotationally locked and slidable in relation to each other, FIGS. 2 and 3.

The device further comprises:—a locking member 96 fixedly connected to the housing and releasably connected to the lead screw member by co-acting locking means;—a first spring force means 48 arranged between the first inner wall 30 of the housing and the nut, wherein the first spring force means is in a pre-tensioned state when said locking means are engaged and the device is in the non-activated state; and—a secondary dose member 90 rotatably connected to said primary dose member 66 via a pinion gear 94, FIG. 3.

The device also comprises dose setting means connected to the primary dose member by co-acting fourth slidably-and-rotatably-locked means, such that when the device is to be set from the non-activated state to the activated state, the dose setting means are manually manipulated in a pre-determined direction, whereby the locking means are released and the lead screw member is distally moved a pre-determined distance by the first spring force means independent of the size of a dose to be set.

Figure 4:
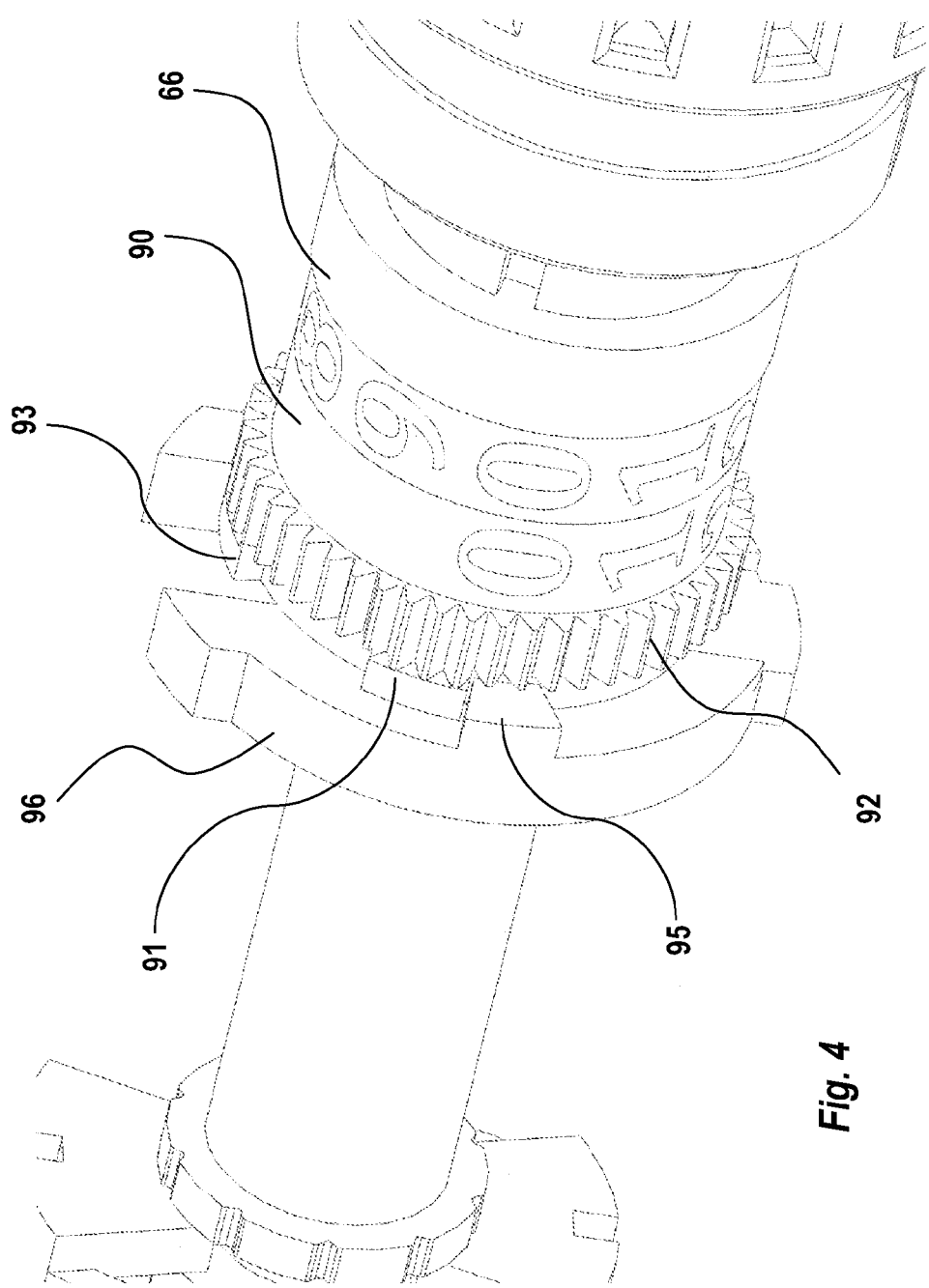
FIG. 4 is a further detailed view of the dose-setting mechanism comprised in the present invention.
Figure 5:
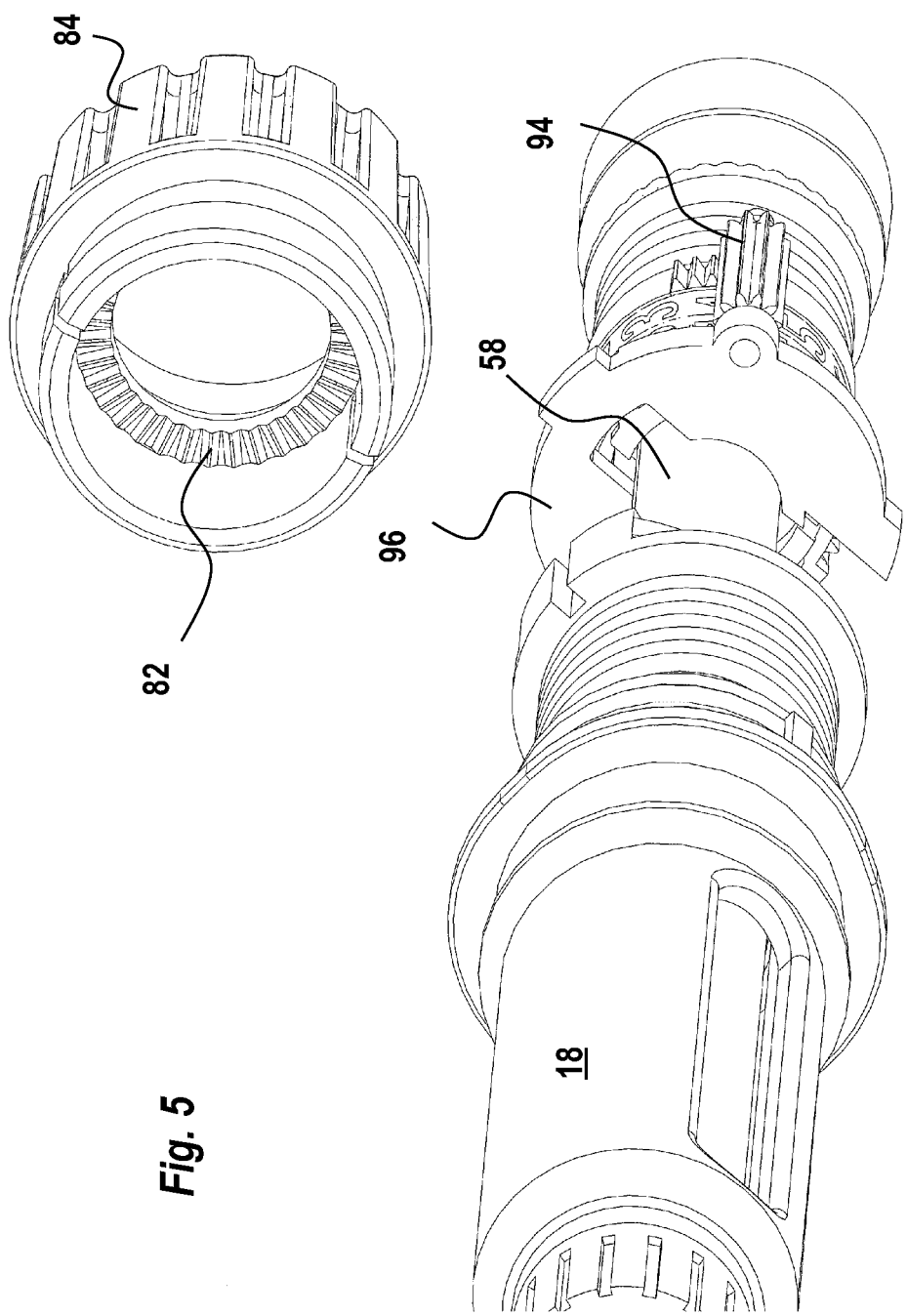
FIG. 5 is yet a further detailed view of the dose-setting mechanism comprised in the present invention.
Figure 6:
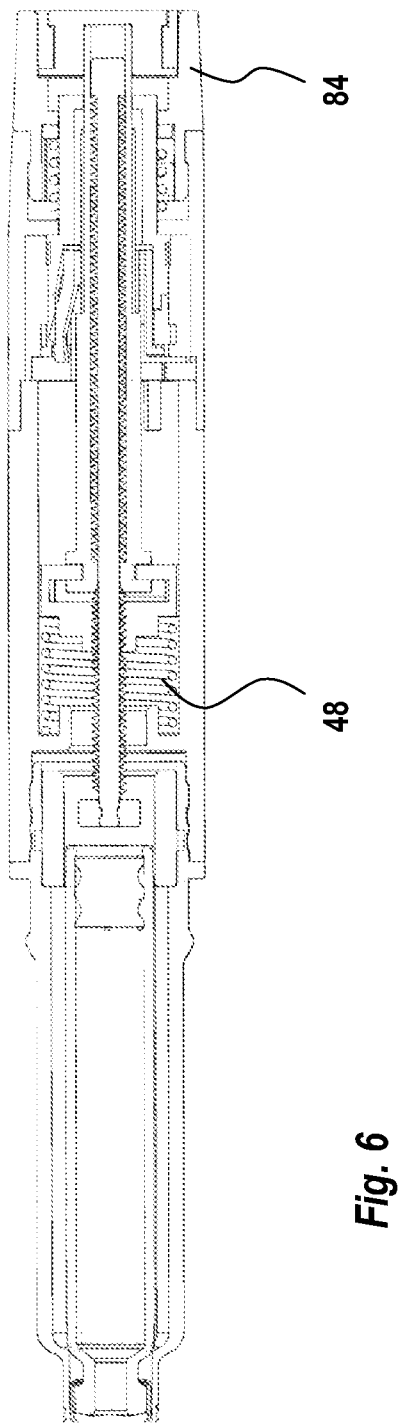

The dose setting means comprises a clutch plate 74 provided with a first annular ratchet 76, a dose setting knob 84 provided with a second annular ratchet 82, and a second spring force means 78 arranged between a second annular inner wall 80 of the housing and a proximal surface of the clutch plate, such that clutch plate is distally urged and the first and the second ratchet are abutting each other, and which dose setting knob protrudes through the distal end of the housing, FIGS. 1a and 4. The fourth slidably-and-rotatably-locked means comprises longitudinally extending grooves 70 on the outer circumferential surface of the primary dose member 66, and radial inwardly directed protrusions 72 on the inner surface of the clutch plate 74, wherein the longitudinally extending grooves 70 cooperate with radial inwardly directed protrusions 72 such that the primary dose member and the clutch plate are rotationally locked and slidable in relation to each other, FIGS. 2 and 3. The distal end of the lead screw member 58 protrudes through the dose setting knob 84, and is at its distal end arranged with a dose injection button 86, FIGS. 2 and 7b. Outside the dose injection button 86 a spin ring 88 is rotatably arranged, FIG. 2.

The locking means comprises:—a proximally pointing and radial flexible lever 102 arranged on the locking member,—an annular ledge 62 on the circumferential surface of the lead crew member, and—the circumferential inner surface of the secondary dose member, FIG. 2. The secondary dose member 90 is also arranged with teeth 92 arranged around its circumference, which teeth cooperate with teeth on the pinion gear 94, which is journalled in the housing as well as the locking member 96 via a locking lever bracket, FIG. 3. Further the primary dose member 66 is arranged with a gear segment 98, which also cooperate with the pinion gear 94, FIG. 3. A certain part of the lead screw member 58 is arranged with the splines 60 on its outer circumferential surface, FIG. 2; which splines have a lesser diameter than the proximal part of the lead screw member, thereby creating the annular ledge 62, FIG. 2. The locking member 96 also comprises on its distal circumferential surface a distally pointing stop member 95, and the secondary dose member 90 comprises on its proximal circumferential surface a first 91 and a second 93 proximally pointing stop member arranged to interact with the stop member of the locking member, FIG. 4.

The proximal part of the primary dose member 66 and the secondary dose member 90 are arranged with a circumferential band containing numbers or indicia 68 which are used to indicate dose size through a dose window on the housing, as will be explained below, FIG. 3.

The device is intended to function as follows. When delivered to the user, the device is in the non-activated state wherein a medicament container 20 has been inserted in the medicament container holder 18 in the proximal end of the device, FIG. 1, the first spring force means is in a pre-tensioned state and said locking means are engaged, wherein the circumferential inner surface of the secondary dose member 90 forces the flexible lever 102 radial inwardly in contact with the ledge 62.

When the device is to be used the protective cap 26 is removed and the dose setting means are manually manipulated for setting the device from the non-activated state to the activated state by rotating the dose setting knob 84 counter clockwise until activating indicia as e.g. two zeros are visible through the window of the housing. The rotation of the dose setting knob 84 causes the clutch plate 74 and thereby the primary dose member 66 to rotate due to the engagement between the co-acting fourth slidably-and-rotatably-locked means, and due to the connection between the first 76 and the second 82 ratchets. However, the lead screw member is not rotated since the third slidably-and-rotatably-locked means 60, 64 are not in engagement, i.e. the splines 60 on the outer circumferential surface of the lead screw member and the corresponding splines 64 arranged on the inner circumferential surface of the primary dose member 66 are not in engagement. The secondary dose member 90 also rotates due to the connection between the gear segment 98 of the primary dose member 66 and the teeth 92 of the secondary dose member 90 through the pinion gear 94. The rotation of the secondary dose member 90 is stopped when its second proximally pointing stop member 93 abuts the distally pointing stop member 95. This causes a longitudinal groove on the inner circumferential surface (not shown) of the secondary stop member to be aligned with the flexible lever 102 whereby the flexible lever is radial outwardly flexed into the groove and thereby moved out of contact with the ledge 62 of the lead screw member 58. This causes the lead screw member 58 to move a pre-determined distance in the distal direction due to the force of the spring 48 acting on the nut 44, which in turn is attached to the lead screw member 58. The splines 60 on the outer circumferential surface of the lead screw member and the corresponding splines 64 arranged on the inner circumferential surface of the primary dose member are then engaged to each other. Because of the movement of the nut 44, the plunger rod 36 is also moved. The distal end of the lead screw member 58 and its dose injection button 86 now protrude distally out of the housing said predetermined distance and independent of the size of the dose to be set.

The device is now in the activated state and ready for setting a required dose of medicament, FIGS. 7a and 7b.

When setting a dose, the plunger rod is arranged to be proximally moved a distance corresponding to a set dose to be delivered by manually manipulating the dose setting knob.

The dose setting knob 84 is rotated in the clockwise direction which also rotates the primary dose member 66 clockwise indicating the dose that is being dialled. At the same time the primary dose member 66 rotates the lead screw member 58 clockwise due to the engagement between the co-acting third slidably-and-rotatably-locked means 60, 64; and the lead screw rotates the plunger rod due to the engagement between the co-acting first slidably-and-rotatably-locked means, driving the plunger rod 36 through the nut 44 because of the threaded engagement between them, thereby moving the plunger rod 36 proximally. The secondary dose member 90 also rotates due to the connection between the gear segment 98 of the primary dose member 66 and the teeth 92 of the secondary dose member 90 through the pinion gear 94. The rotation of the secondary dose member 90 is stopped when its first proximally pointing stop member 91 abuts the distally pointing stop member 95, which indicates the maximum dose the device can deliver e.g. two indicia as e.g. a seven and a zero are visible through the dose window. In any case, the set dose is visible through the dose window of the housing. At this point the device is ready for an injection.

Moreover, if the user attempts to dial past the maximum dose the device can deliver or if the user attempts to dial pass the activating indicia, the connection between the first annular ratchet 76 and the second annular ratchet will function as a clutch.

When the dose is set, a medicament delivery member 24 is attached to the proximal end of the device, such as e.g. an injection needle. It is however to be understood that other types of medicament delivery members may be used in order to deliver a dose of medicament. The medicament delivery member is then placed at the delivery site and the user presses the dose injection button 86 in the proximal direction the predetermined distance that the distal end of the lead screw member 58 and its dose injection button 86 protrudes distally out of the housing and which said predetermined distance is independent of the size of the dose to be delivered. This causes the lead screw member 58 to move in the proximal direction as well as the nut 44 and the plunger rod 36. This proximal movement of the plunger rod 36 causes it to act on the stopper 38 of the medicament container 20 whereby a dose of medicament is expelled through the medicament delivery member 24. When the lead screw member 58 has reached a certain distance inside the housing, the flexible lever 102 of the locking member is again moved in contact with the ledge 62 of the lead screw member 58, FIG. 8. The medicament delivery member may now be removed and discarded.

When a subsequent dose is to be performed, the above described procedure is performed and can be repeated until the medicament container is emptied.

It is to be understood that the embodiment described above and shown in the drawings is to be regarded only as a non-limiting example of the invention and that it may be modified in many ways within the scope of the patent claims.

The invention claimed is:

1. A does setting mechanism for a medicament delivery device comprising,
   a housing having a longitudinal axis;
   a lead screw configured to rotate and move axially relative to the housing;
   a locking member adjacent the lead screw and configured to be in a non-activated position and an activated position;
   a pinion connected to the locking member and having an axis of rotation offset and parallel to the longitudinal axis; and
   a plunger rotationally fixed to and axially slidable relative to the lead screw,
   wherein the locking member is configured to prevent axial movement of the lead screw in the non-activated position.

2. The dose setting mechanism of claim 1 further comprising a spring configured to be in a pre-tensioned state when the locking member is in the non-activated position, where the spring biases the lead screw and plunger distally.

3. The dose setting mechanism of claim 1 wherein the lead screw further comprises a ledge and the locking member further comprises a lever, wherein the ledge engages the lever when in the non-activated position.

4. The dose setting mechanism of claim 3 wherein the lever is disengaged from the ledge when in the activated position.

5. A does setting mechanism for a medicament delivery device comprising,
   a housing having a longitudinal axis;
   a nut rotationally fixed and longitudinally slidable relative to the housing;
   a spring biasing the nut in a distal direction;
   a locking member configured to be in a non-activated position and an activated position;
   a pinion connected to the locking member and having an axis of rotation offset and parallel to the longitudinal axis;
   a plunger rod threadedly engaged with the nut; and
   a lead screw rotationally fixed to and axially slidable relative to the plunger rod,
   wherein the locking member is configured to allow axial movement of the lead screw in the activated position.

6. The dose setting mechanism of claim 5 where the nut comprises a ratchet arm that cooperates with grooves on the lead screw to produce an audible sound when the lead screw is rotated relative to the housing.

7. The dose setting mechanism of claim 5 where the lead screw has an outer circumferential surface comprising splines oriented parallel to the longitudinal axis.

8. The dose setting mechanism of claim 7, further comprising a primary dose member having an inner surface of splines, wherein the splines of the lead screw cooperate with corresponding splines on an inner surface of a primary dose member to rotationally lock the lead screw to the primary dose member.

9. The dose setting mechanism of claim 8 further comprising a clutch plate rotationally fixed to the primary dose member, where the clutch plate has a first annular ratchet that engages a second annular ratchet on a dose knob.

10. The dose setting mechanism of claim 9 where the dose knob protrudes through a distal end of the housing.

11. The dose setting mechanism of claim 9 where the dose knob is configured to allow a user to set a dose by rotating the knob which simultaneously rotates the plunger rod causing the rod to move axially relative to the nut.

12. The dose setting mechanism of claim 5 wherein the lead screw is configured to move axially in the distal direction the same distance each time the locking mechanism is changed from the non-activated position to the activated position.

13. The dose setting mechanism of claim 5 where the threaded engagement of the plunger and the nut is configured so that rotation and axial movement of the plunger rod relative to the nut is equal to a dose set by a user.

14. The dose setting mechanism of claim 5 wherein rotation of the lead screw to a zero dose position causes the locking mechanism to change from the non-activated position to the activated position.

* * * * *